(12) United States Patent
Defez

(10) Patent No.: US 7,846,708 B2
(45) Date of Patent: Dec. 7, 2010

(54) METHOD FOR INCREASING THE SURVIVAL OF BACTERIAL STRAINS OF THE RHIZOBIUM GENUS

(75) Inventor: Roberto Defez, Rome (IT)

(73) Assignee: Consiglo Nazionale delle Richerch, Rome (IT)

( * ) Notice: Subject to any disclaimer, the term of this patent is extended or adjusted under 35 U.S.C. 154(b) by 0 days.

(21) Appl. No.: 11/917,405

(22) PCT Filed: Jun. 13, 2006

(86) PCT No.: PCT/IT2006/000449

§ 371 (c)(1),
(2), (4) Date: Dec. 13, 2007

(87) PCT Pub. No.: WO2006/134623

PCT Pub. Date: Dec. 21, 2006

(65) Prior Publication Data

US 2010/0035347 A1    Feb. 11, 2010

(30) Foreign Application Priority Data

Jun. 14, 2005   (IT) ................. RM2005A0308

(51) Int. Cl.
*C12N 1/00*   (2006.01)
*C12N 1/20*   (2006.01)
*C12N 1/38*   (2006.01)
*C12N 5/00*   (2006.01)
*C12N 5/02*   (2006.01)

(52) U.S. Cl. .............. 435/243; 435/244; 435/252.1; 435/410; 435/420; 435/431

(58) Field of Classification Search .............. None
See application file for complete search history.

(56) References Cited

U.S. PATENT DOCUMENTS

2005/0070435 A1*   3/2005   Chopade et al. ............ 504/117

OTHER PUBLICATIONS

Tinland et al (Plant Molecular Biology vol. 16, pp. 853-864, 1991).*
De (Acta Biotechnol. vol. 15, No. 3, pp. 307-316, 1995).*

* cited by examiner

*Primary Examiner*—Mark Navarro
(74) *Attorney, Agent, or Firm*—Kenneth K. Sharples

(57) ABSTRACT

The present invention describes a method for increasing the survival of the bacteria of *Rhizobium* genus, comprising the steps of: making the bacteria to grow in a chemically defined medium; keeping the bacteria in growth stationary phase for a proper period of time; exposing the bacteria to effective quantities of indole-3-acetic acid (IAA). Within the invention scope there is an alternative method to increase the survival of the bacteria of the *Rhizobium* genus by means of genetic engineering comprising the steps of: making a recombinant vector codifying enzymes able to produce IAA to express in effective way in said bacteria; making the bacteria to grow in chemically defined culture medium; keeping the bacteria in growth stationary phase for a proper period of time.

8 Claims, 11 Drawing Sheets

Fig.1bis

Figure 1:
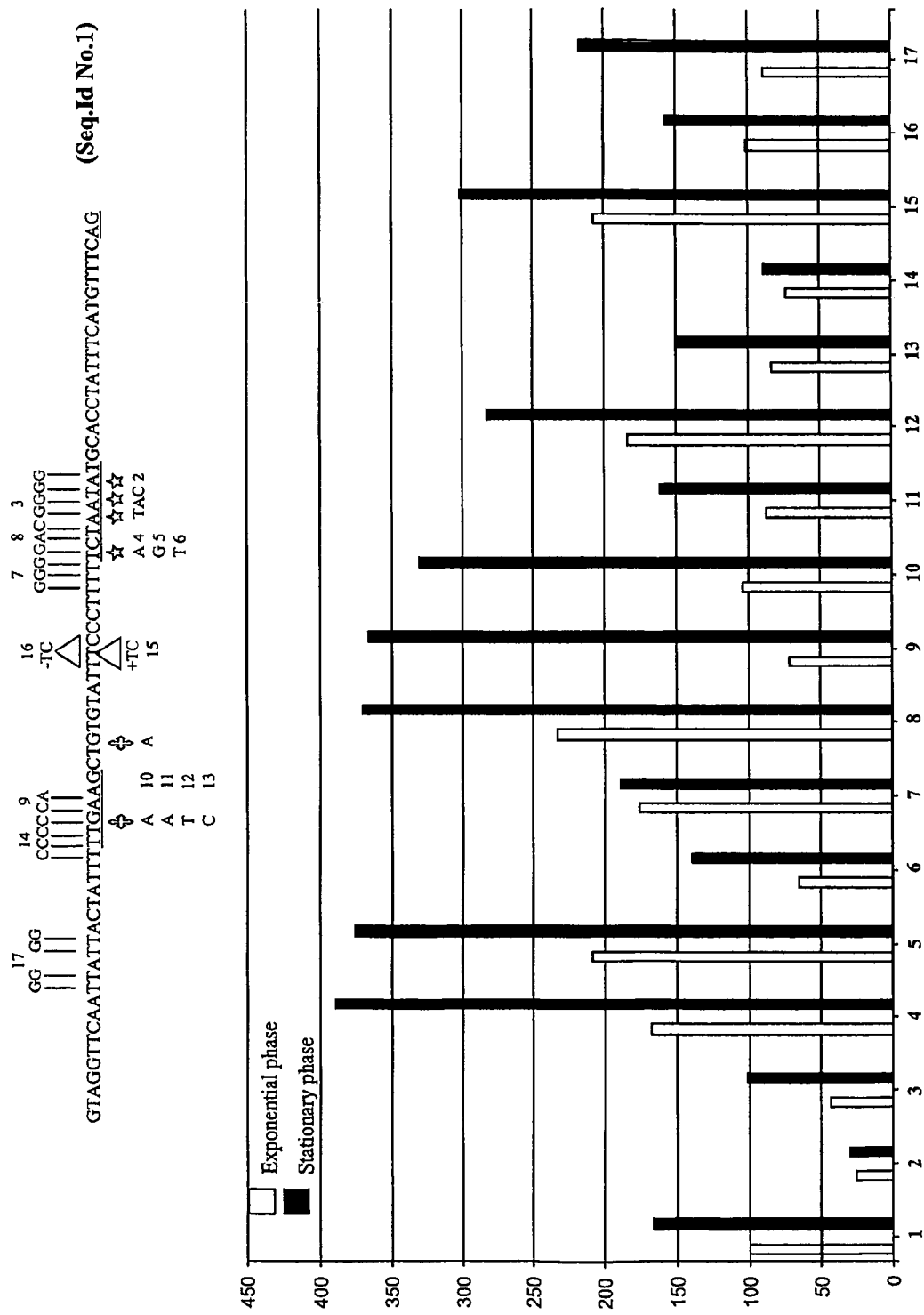

Bold:promoter
underlined: iaaM
*Italic: tms2*

(Seq.Id.No.2)

```
GTAGGTTCAATTATTACTATTTTGAAGCTGTGTATTCCCTTTTCTAATATGCACCTATTTCATGTTTCAGGGGTAGGTCAGTCCCTTGGTACCC
AAGAATCGTAATCCGGTAGCACGTAAGGTCGAAGAGGTAGAGGGTAGAGTCGCGTATGTGACCATTTTAATCACCCAGTATTGATATTTGTACGA
CTACGGTCCCTTTCTGAAAAAATGTGAACTCGTCGCTGCAACAGACCTATTCAGCCGGAAGCGCCCACCCTTGGGTAGGGTAGTGCGGTGCC
GGCATCAGTGGGCTGGTCGCTGCAACAGACTGTCTGCACATTGCGCGGGAGTCAAGGACGTTGTCTTATATGAATCGTGATCAACTGGGGGACGGG
TATGGTCTCAAGTTTTGGTATTTCGACGTCGACCACCCTTTCCGGATCCTGGTGTGGTGGCAGTCTCTATTGTCCGAAGGTACCTCTTGAAGCGGTCTTAGT
TGAAAAAGTTTGGTATTCGACGTCGACCACCCTTCCGGATCCTGGTGGGAGCCGCAATTATTCCGGATCCAATGCGAGGATCGATCGATCGATC
GCGGGCAAAAAGCCGCCGAATTATTCAGGCGAGTCGGGTGCAGCTCTATGAGGGATGGGCTCTCTGAAGAGGCAGGATGCTCATGTATTCCGGATGT
TGCCCCGCTGGACATTACCGCGATTGTCTGTATTTACTGCCGTAGCGCGGGTTTTTGCCAGTCTTCAGGTCTTCAGGCTCGGCGCCATCGCCCAGGCGGCCTAGCCGG
TCATTCTATAACGCGATTGTCTGTATTTTACTGCCAGTCTGCCCGAGAACTCGCTGATCAGTCGTTTGACGGCAAGCGTTATTTGATCGAGTAATTGTCACTAGCAGTA
GCTTGGCATAGCTCGGGACGGATATCCAGTCTGCCCGAGAACTCATCGAGAGCTTCTGAGTCGTGATGTCGCTGATCAGTCGTTTGATCGAGTAATTGTCACTAGCAGTA
GACTGATTCCGGACGGGATATCCAGTCTGGGCCCGAGAACTCATCCAGAGCAAGCTTCTGAGTCGTGATGTCGCTGATCAGTCGTTTGATCGAGTAATTGTCACTAGCAGTA
GGTAGGCCGCATTCCAGAGAAGCTCACTGCCTCACCCGAACCAATTCTGGATAAAAAACAAGCTTCTGCTCAGTTACACGTGGAAGACGAGCGCTCAAAAATGTGGCGATGC
ATCGGGCCATGCAATGCTTTCATTCTCACCCGATGAACCTGCCAGGTACTGGGTGTCACCATGCCACCATGACAGCGGTTATTCAACCAGATTACCATCCGAGACGCGCTATATCGGGATATGCGAGGGATTAT
TGTCTGGATATCAGCCCGATGAACCTGCCAGGTACTGGGTGTCACCATGACAGCAGCAATTGAACAGTGCCTCTATCTGCCGCGTTACTCGCAGCG
CTGACAAGAAAACGCGTTGCACCATGACAGCAGCAATTGAACAGTGCCTCTATCTGCCGCGTTACTCGCAGCG
GAGCGGTATGTATTCAACCAATGACAGCAGCATTGAACAGTGCCTCTATCTGCCGCGTTACTCGCAGCG
ATTGTTTTTTCAACCAATGACAGCAGCATTGAACAGTGCCTCTATCTGCCGCGTTACTCGCAGCG
AAGGTCTGTCCAGACAGCATTAACAGTCCTGAGAGCAGCAGCTAAGCTAATACGGGTCAAAAGAGCATGCtgcagtcgactctaagacaccagagagatggtgc
CGCCTCCTATCGCTATGCTATTAACAGTCCTGAGAGCAGCAGCTAAGCTAATACGGGTCAAAAGAGCATGCtgcagtcgactctaagacaccagagagatggtgc
cattacctcgttagcccaaagcctagaacgtgaaacgtagaaacctgataagcaccgaagaaccttcgggcatctcggcttagaacctgatagaacctgatagaacctgatagaccttcggctacagactgggatggtttg
cggcgaagcgccaaaaaattgatcgctgtgcagaaaaaaatctcgcagaagacttttttcagctggaagcactggcctcggagtgtgctgccaagcgccgggtgcggacgtcgtgcaccgtcgtcagcgggcgacccgtgga
gccaaagataccatcccgcgtgcgcagaaaaaaatctcgcagaaaacgcttggcggttgcaccgataccggtcctgccatcgttcgt
atccagatcgataccagggggtctcaagcggtGGTGTGCGTAGTAGGATTTCGACGACGCCTTGGACCGGAGATCGGATATCCGGAGATCGGGCTAGCCTAGCCTACCCGGAC
CTACCCCGCAGCCGTGGTGTGCGTAGTAGGATTTCGACGACGCCTGAACCTGTAATCCTCGACCGGATATGTTGTAATATGATGCTGATGTGCCCTAGCAGTCGCAGCCTATACCACCGTCGCCTGA
ACTCCCGGAATCATAGCGGTGCCCTACAACTACCTGGTCTGCGTAGGCGGTGTGAATCCTCGACCTGTAATCCTCGACCTGTAATGATGCTGATGTGCCCTAGCAGTCGCAGCCTATACCACCGTCGCCTGA
AGGGCTAAGGATCGGCGTGCCCTACAACTACTTTTATGATGACCTTGATGCTGATGTGCCCTAGCAGTCGCAGCCTATACCACCGTCGCCTGA
AACAAGGCTAAGCTTTTCTTGTTGAAGCTAACCTGCATTCCCCACCTTGACGAACCTGAATAAAGGGCCAGCCAGCTTTCCCAGTTTCAGCAGCTTCGAATTCCACAC
GCTCTAAACGTATCTCGACGACCTTTGTAAAACGTGTTTCTTTCTGACGTCATCAAGGAATTCGTAGCGTGATGTAGTCAACATTGCCAATG
CGCAAATTGATGGACATCAAATTTCCAAGCTGAATGAACTGGCCCGCCACCTCCTTCAGACCAAGACTTCAAGCCCACTCAGTTATCCGAACTACTTC
AACTGAATAGATTAGAATCGATGCTATTCTCTACGTGCGAAATGTGACCCAAGCAACCAGCCTACCTGGCttgagcattccgtttgcctgacaactgatcgctgtttggaatgg
CTGGACACATTCAGAATTCGATGCTACGTGCGAAATGTGACCCAAGCAACCAGCCTACCTGGCttgagcattccgtttgcctgacaactgatcgctgtttggaatgg
agatcgatgattagcgattagcaacgtgtagcaacgtctgtggggggcattgcaatcggattccgatattttgccggtttaccccaattaacATCAAGCTTGATATCGAATTCCTGCA
GCCCGGGATCCACTAGTTCTAGAGCGGCCGCCACCGCGGTGGAGCTCCAACTTAATCGCCTTGCAGCACATCCCCCTTTGCCCAGCTGGCGTAAGATCCAT
TCGTTTACAACGTCGACTGGGAAACCCCTGGCGTTACCCAACTTAATCGCCTTGCAGCACATCCCCCTTTGCCCAGCTGGCGTAAGATCCAT
CAGGCAACGACGGGCTGCTGCCGGCCATCAGCGACGAGGG
```

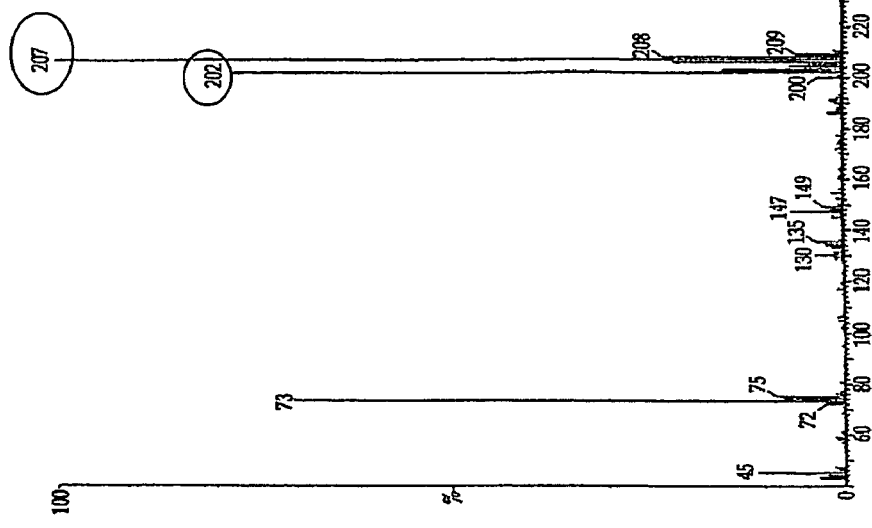
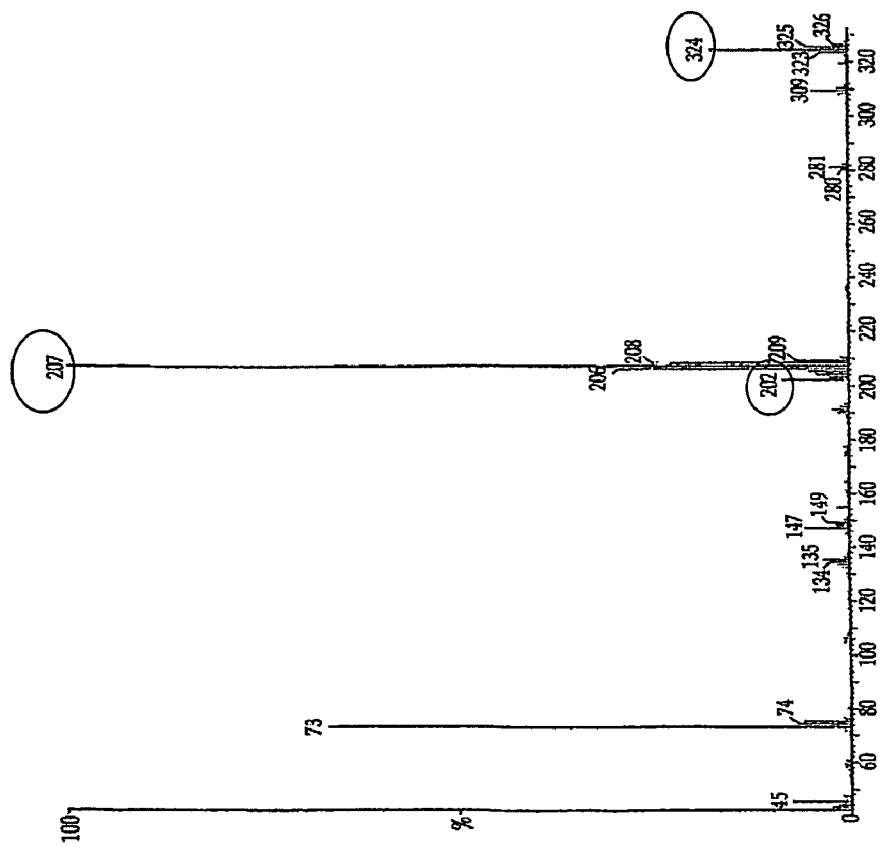
Fig.3

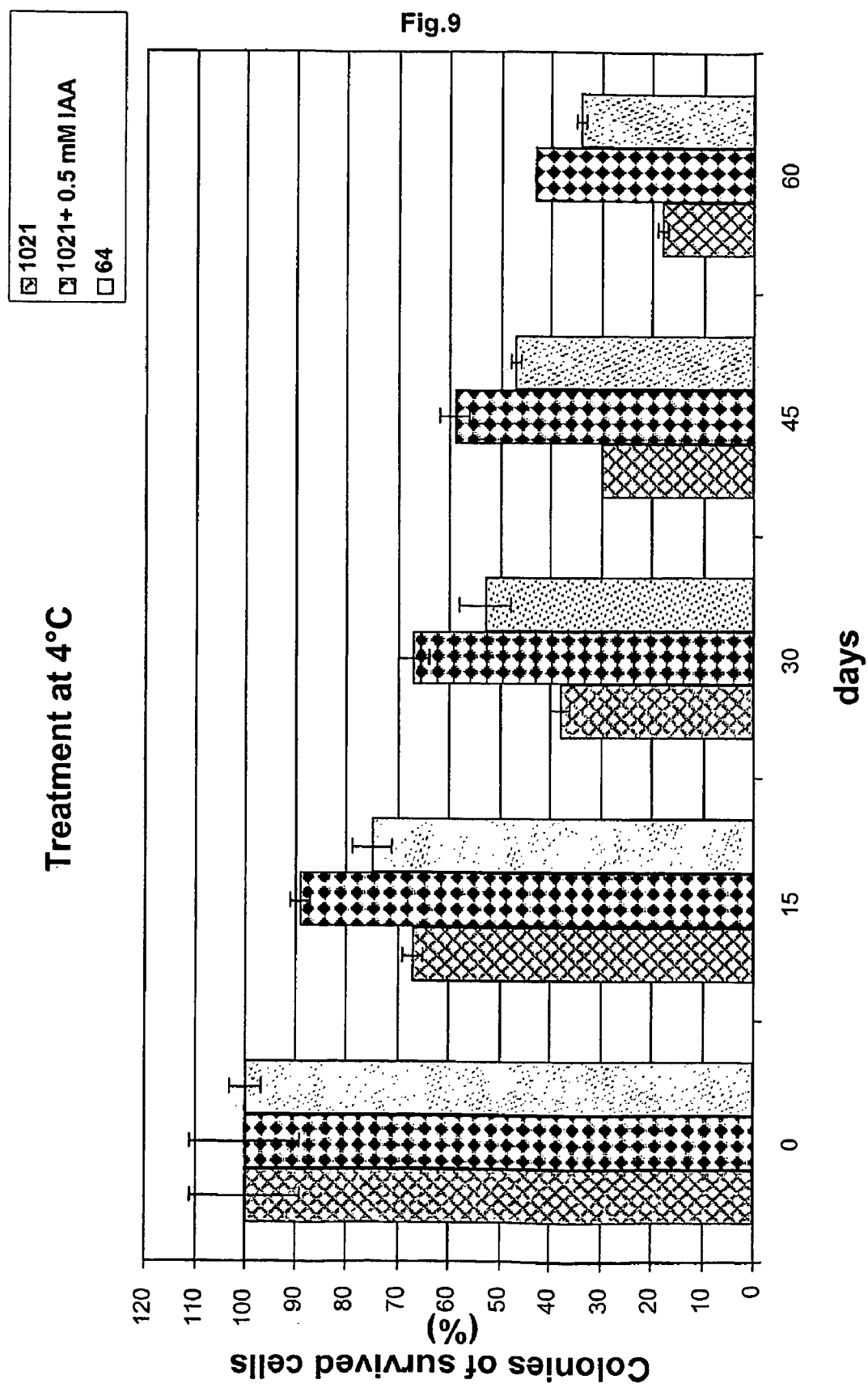

SEQUENCE LISTING

<160> NUMBER OF SEQ ID NOS: 6

<210> SEQ ID NO 1
<211> LENGTH: 73
<212> TYPE: DNA
<213> ORGANISM: Rhizobium sp.

<400> SEQUENCE: 1

| | |
|---|---|
| gtaggttcaa ttattactat ttttgaagct gtgtatttcc cttttctaa tatgcaccta | 60 |
| tttcatgttt cag | 73 |

<210> SEQ ID NO 2
<211> LENGTH: 3567
<212> TYPE: DNA
<213> ORGANISM: Rhizobium sp.

<400> SEQUENCE: 2

| | |
|---|---|
| gtaggttcaa ttattactat ttttgaagct gtgtatttcc cttttctaa tatgcaccta | 60 |
| tttcatgttt caggggtagg tcagtccctt ggtacccaaa gaatcgtaat ccgggtagca | 120 |
| cgtaaggtcg aagagggtag agtcgcgtta tgtatgacca ttttaattca cccagtattg | 180 |
| atattttgta cgactacggt cccttttctga aaaaatgtga atgacgggga ggcataggca | 240 |
| gctattcagc cggaacgccc acccctcggg tagcgatagt cggtgccggc atcagtgggc | 300 |
| tggtcgctgc aactgaacta ttacgtgcgg gagtcaagga cgttgtctta tgaatcgc | 360 |
| gtgatcgaat cggggacgg gtatggtctc aagttttcga tcagactcgt ccacgttaca | 420 |
| ttgcagaaat gggtgcgatg cgcttcctc ccagtgcaac tggccttttc cactacctga | 480 |
| aaaagtttgg tatttcgacg tcgaccacct ttccggatcc tggtgtggtg gacacggagc | 540 |
| tgcattaccg tggcaagcgc tatcactggc agcgggcaa aaagccgccc gaattattca | 600 |
| ggcgagtcta tgagggtgg cagtctctat tgtccgaagg ttacctcctt gaaggcggtt | 660 |
| ctttagttgc cccgctggac attaccgcaa tgctgaagtc gggtcgtctg gaagaggcag | 720 |
| cgatcgcatg gcagggatgg ctcaatgtat tccgggattg ttcattctat aacgcgattg | 780 |
| tctgtatttt tactggccgc catccgccag gcggcgacag atgggctcgt cctgaagact | 840 |
| ttgagctgtt tggctcgctt ggcataggct cgggcgggtt tttgccagtc tttcaggctg | 900 |
| gctttacgga aatactgcgg atggttatca acggatacca aagtgaccag cgactgattc | 960 |
| cggacgggat atccagtctg gccgcgagac tcgctgatca gtcgtttgac ggcaaagcgt | 1020 |
| taagggaccg cgtttgtttt agccgggtag gtcgcatttc cagagaagct gaaaaaatca | 1080 |
| tcatccagac ggaagcagga gaacagcgtg tatttgatcg agtaattgtc actagcagta | 1140 |
| atcgggccat gcaaatgatt cactgcctca cggatagcga gagctttctg agtcgtgatg | 1200 |
| tcgctcgtgc tgtccgcgaa acccatctga caggttcatc gaagcttttc attctcaccc | 1260 |
| gaaccaaatt ctggataaaa aacaagcttc ccaccaccat ccagtcggac ggtctggtgc | 1320 |
| gcggcgtcta ttgtctggat tatcagcccg atgaacctga gggcatggc gttgttctgc | 1380 |
| tcagttacac gtgggaagac gacgctcaaa aaatgctggc gatgcctgac aagaaaacgc | 1440 |
| gttgccaggt actggttgat gaccttgctg cgatacaccc gacgttcgcc agttatctcc | 1500 |
| tgcccgttga tggggattat gagcggtatg tattgcacca tgactggctc accgatcccc | 1560 |
| attctgcggg cgcttccaaa ctcaattatc ccggcgagga cgtttactcg cagcgattgt | 1620 |
| ttttcaacc aatgacagcg aacagtccca ataaagacac ggggctctat ctggctggct | 1680 |

-continued

```
gcagttgctc ttttgccgga gggtggatcg aaggtgctgt ccagacagca ttgaacagtg      1740
cttgcgcggt gctgcgcagc accggagggc aactgtcaaa aggcaacccg ctggactgta      1800
tcaacgcctc ctatcgctat taacagtcct gagagcagcg ctaagctaat acgggtcaaa      1860
agagcatgcc tgcaggtcga ctctagagga tccaactcag agagatggtg gccattacct      1920
cgttagccca aagcctagaa cacctgaaac ggaaagacta ctcctgctta gaactagtag      1980
aaactctgat agcgcgttgt gaagctgcaa aatcattaaa cgcccttctg gctacagact      2040
gggatggttt gcggcgaagc gccaaaaaaa ttgatcgcca tggaaacgcc ggagtaggtc      2100
tttgcggcat tccactctgt tttaaggcga acatcgctac cggcgtattt cccacaagcg      2160
ccgctacgcc ggcgctgata aaccacttgc caaagatacc atcccgcgtc gcagaaagac      2220
ttttttcagc tggagcactg ccgggtgcct cgggaaatat gcatgagtta tcgtttggaa      2280
ttacaagcaa caactatgcc accggggcgg tgcgaaaccc gtggaatcca gatctgatac      2340 caggggggctc aagcggtggt gtggctgctg cggtagcaag ccgattgatg ttaggcggca      2400
taggcaccga taccggtgca tctgttcgcc tacccgcagc cctgtgtggc gtagtaggat      2460
ttcgaccgac gcttggtaga tatccgggag atcggataat accggttagc cctacccggg      2520
acactcccgg aatcatagcg cagtgcgtag ccgatgttgt aatcctcgac cggataattt      2580
ccggcacacc ggagagaata ccacccgtgc cgctgaaggg gctaaggatc ggcctcccta      2640
caacctactt ttatgatgac cttgatgctg atgtggccct agcagctgaa acaacgattc      2700
gcctgctagc aaacaaaggc gtaacttttg ttgaagctaa cattccccac cttgacgaac      2760
tgaataaagg ggccagcttc ccagttgcac tctatgaatt ccacacgct ctaaaacagt       2820 atctcgacga ctttgtaaaa actgtttctt tttctgacgt catcaaagga attcgtagcc      2880
ctgatgtagc caacattgcc aatgcgcaaa ttgatggaca tcaaatttcc aaagctgaat      2940
atgaactggc ccgccactcc ttcagaccaa gacttcaagc ccacctatcg caactacttc      3000
aaactgaata gattagatgc tattctcttc ccaacagcac ccttggtggc cagacccata      3060
ggtcaggatt cctcagttat ccacaatggc acgatgctgg acacattcag aatctacgtg      3120
cgaaatgtgg acccaagcag caacgcaggc ctacctggct tgagcattcc tgtttgcctg      3180
acacctgatc gcttgcctgt tggaatggag atcgatggat tagcggattc agaccaacgt      3240
ctgttagcaa tcgggggggc attggaagaa gccattggat tccgatattt tgccggttta      3300
cccaattaaa catcaagctt gatatcgaat tcctgcagcc cggggatcc actagttcta       3360 gagcggccgc caccgcggtg gagctccaat tcgccctata gtgagtcgta ttacgcgcgc      3420
tcactggccg tcgttttaca acgtcgtgac tgggaaaacc ctggcgttac ccaacttaat      3480
cgccttgcag cacatccccc tttcgccagc tggcgtaaga tccatcaggc aacgacgggc      3540
tgctgccggc catcagcgga cgcaggg                                          3567
```

<210> SEQ ID NO 3
<211> LENGTH: 85
<212> TYPE: DNA
<213> ORGANISM: Rhizobium sp.

<400> SEQUENCE: 3

```
gtgagtgtgg ttgtaggttc aattattact attttttgaag ctgtgtattt ccctttttct     60
aatatgcacc tatttcatgt ttcag                                            85
```

<210> SEQ ID NO 4

```
<211> LENGTH: 85
<212> TYPE: DNA
<213> ORGANISM: Rhizobium sp.

<400> SEQUENCE: 4
gtgagtgtgg ttgtaggttc aattattact atttttgaag ctgtgtattt cccttttttga    60 catatgcacc tatttcatgt ttcag                                           85

<210> SEQ ID NO 5
<211> LENGTH: 85
<212> TYPE: DNA
<213> ORGANISM: Rhizobium sp.

<400> SEQUENCE: 5
gtgagtgtgg ttgtaggttc aaggaggact atttttgaag ctgtgtattt cccttttttct    60 aatatgcacc tatttcatgt ttcag                                           85

<210> SEQ ID NO 6
<211> LENGTH: 85
<212> TYPE: DNA
<213> ORGANISM: Rhizobium sp.

<400> SEQUENCE: 6
gtgagtgtgg ttgtaggttc aattattact atttccccag ctgtgtattt cccttttttct    60 aatatgcacc tatttcatgt ttcag                                           85
```

METHOD FOR INCREASING THE SURVIVAL OF BACTERIAL STRAINS OF THE RHIZOBIUM GENUS

The present invention relates to a method for increasing the growth ability and/or the survival time of bacteria belonging to the *Rhizobium* genus by means of exposition and/or endogenous production of effective quantities of indole-3-acetic acid (IAA). In particular, the method is advantageous for obtaining bacteria of the *Rhizobium* genus with increased survival, which can be used as dried product, for treating seeds of leguminous plants. The IAA is added to the outer medium or it is produced by biosynthetic pathway from the bacterium itself by means of techniques of genetic engineering.

The author of the present invention has defined the proper IAA concentration range to be added in solution to the growth medium or, as alternative, he has engineered the promoter of the coding genes for an indoleacetamide hydrolase (iaaM) and a tryptophan monooxygenase (tms2) which convert the tryptophan into IAA via indoleacetamide, in order to detect the proper conditions.

The method allows obtaining inocula for the bacterization of the most vital and then more effective seeds of leguminous plants. In fact, the bacteria treated with the method of the invention have a greater probability to meet the roots of the leguminous plants, which is a necessary condition in order to have a nitrogen-fixing nodulation.

The author has evaluated the resistance and the survival of the various bacterial strains under dehydration conditions.

Such condition has particular importance to the application purposes, since the bacterial inoculum under the form of dry pulp is used to cover the legumes' seeds according to a "coating"-defined process. In such way, once planted and rehydrated, the seed will be in contact with a very high quantity of bacteria of the *rhizobium* strain which one wishes come in contact with that particular leguminous plant. The seeds covered with dehydrated bacterial pulp are prepared some weeks before the seeding and therefore the bacterial vitality is a very appreciated parameter.

Finally the author showed that *Rhizobium* cells treated with or synthesizing IAA are more resistant to a number of environmental and physical stress such as low pH, high osmotic pressure, low and high temperature and exposition to UV light. Globally taken this increased resistance to stress conditions might favor the survival of the bacteria in the soil thus enhancing the possibility of a successful interaction between legumes and nitrogen fixing bacteria.

PRIOR ART

The soil bacteria of the *Rhizobium* genus are able to break the triple bond of the atmospheric nitrogen molecule when they are in association with the roots of the leguminous plants (Brill). Under such conditions the plant yields to the energetic bacterial compounds, such as the malate dicarboxylic and succinic acids deriving from the chlorophyllous photosynthesis, by creating at the same time a reducing environment, that is with oxygen partial low pressure. Under such conditions the bacterium synthesizes the multi-enzymatic nitrogenase complex which reduces the atmospheric nitrogen to ammonium.

The no more inert nitrogen under the N2 form, but reduced to ammonium or urea by the bacteria is then yielded to the plant which in this way obtains a great advantage with respect to any other living organism, since only leguminous plants are able to assimilate nitrogen directly from the atmosphere in order to convert it into all the organic molecules necessary for life.

Each leguminous plant establishes symbiosis with one or with very few *Rhizobium* genera then in the industrial cultivations of leguminous plants, in order to increase the meeting probability between the germinating seed (soya, trifolium, lupine, lucerne, pea, etc.) and a particular type of bacterium, the latter are inoculated with very high doses (hundred millions bacteria per single seed). This takes place in several areas of the world since the rhizobia often do not succeed in surviving in the soils and if they are not added at time of feeding the plants will need synthesis nitrogenous fertilizers. Furthermore, some companies producing inocula for the bacterization of the leguminous seeds have selected particular bacterial strains which are able to better favour the vegetable in the soil, one tries to favour the meeting between a leguminous plant and a particular strain of *rhizobium*. In order to favour such meeting, it is fundamental that the added bacterial charge be high, that is that the number of live bacteria added with the seed be two-three orders of magnitude higher than the indigenous bacterial charge of the soil, generally between $10^3$ to $10^4$ rhizobia per gram of cultured medium.

Furthermore, the scientific literature shows that the phytohormones play a key role in the development of the root nodule (Hirsch et al.) but, up to day, the IAA role in such process is not known.

Therefore, it is evident the need to develop a system able to increase the survival of the rhizobia to be used as dried product in order to optimize the nodulation yield and to reduce the environmental pollution by using a method alternative to the nitrogenous fertilizers.

The patent application PCT/IT99/00355 describes a bacterium containing a recombinant plasmid able to express the iaaMtms2 genera. However, the application does not show nor suggest if such bacteria have an increased growth ability and/or a longer survival time.

SUMMARY OF THE INVENTION

Therefore, the object of the present invention is a method for increasing the survival of bacteria of *Rhizobium* genus, comprising the steps of:
a) making the bacteria to grow in a chemically defined medium;
b) keeping the bacteria in growth stationary phase for a proper period of time;
c) exposing the bacteria to effective amounts of indole-3-acetic acid (IAA).

Preferably the bacteria are kept in growth stationary phase for at least 48 hours.

Preferably the IAA concentration in the medium is comprised between 0.05 mM and 2 mM.

Within the object of the invention there is an alternative method to increase the survival of the bacteria of the *Rhizobium* genus by means of genetic engineering comprising the steps of:
a) transform said bacteria with a recombinant vector codifying enzymes able to produce IAA and effectively expressing them;
b) making the bacteria to grow in chemically defined culture medium;
c) keeping the bacteria in growth stationary phase for a proper period of time.

Preferably the bacteria are kept in growth stationary phase for at least 48 hours.

Preferably the enzymes able to produce IAA are the indoleacetamide hydrolase (iaaM) and the tryptophan monooxygenase (tms2).

In a preferred embodiment the bacteria of the Rhizobium genus belong to the R.l. viciae or S. meliloti species.

The bacteria of the Rhizobium genus treated with one of the described methods are an additional object of the invention.

The use of such bacteria for the preparation of inocula for the bacterization of leguminous seeds is an additional object of the invention.

A dehydrated coating of bacteria of the Rhizobium genus obtainable with the described method is an additional object of the invention.

In order to analyse the survival ability of the rhizobia, the author has used the bacterial strain Sinorhizobium meliloti 1021 as reference strain, able to nodulate lucerne plants and so far the only rhizobium strain fully sequenced (Galibert et al.).

The present invention will be now described in not limiting examples, with particular reference to the following figures:

FIG. 1: Effect of the mutations in the sequence of the promintron of the GUS gene reporter on the β-glucuronidase activity thereof derived from the uidA gene in R.I. viciae, LPR1105.

The nucleotidic sequence of here described 86 bases correspond to the wild type promoter (Seq. Id. No.1) and the whole sequence derived from the iudA gene in R.I. viciae is shown in FIG. 1 bis (Seq.Id.No 2). The sample 1 is the promintron-GUS control. All other samples (2 to 17) correspond to the relative mutations shown in the upper part of the figure. The mutated bases, underlined with a number, are tabulated at the base which they replace. Each time the GUS activity in exponential (column on the left) and stationary (column on the right) phase has been evaluated. The GUS activity of the sample 1 in growth exponential phase is arbitrarily placed equal to 100%.

Figure 2:
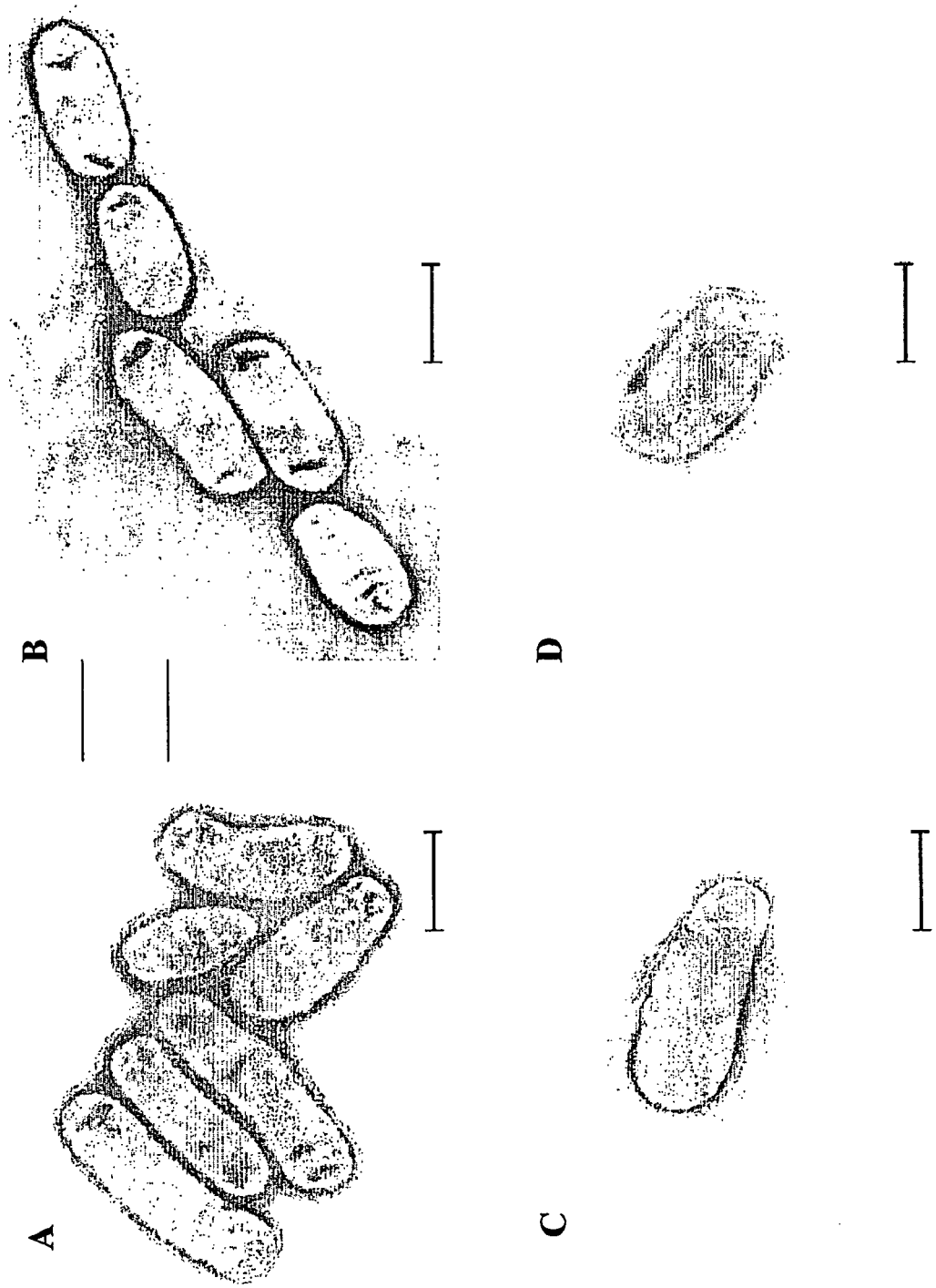

FIG. 2: Electronic microscopy of free-living bacteria of the wild-type strains of R.l. viciae LPR 1105 (A) and of S. meliloti 1021 (C) and of the corresponding strains RD20 (B) and RD64 (D) transformed with the promintron-iaaMtms2 construct. Bars, 1 μm 10,000×.

FIG. 3: Online chromatography gas spectrum with mass spectrometry (GC/MS) of supernatants of the bacterial strains LPR 1105 and RD20 grown in exponential phase. The peaks related to the integral (319 or 324) or fragmented (202 or 207) IAA are encircled.

Figure 4:
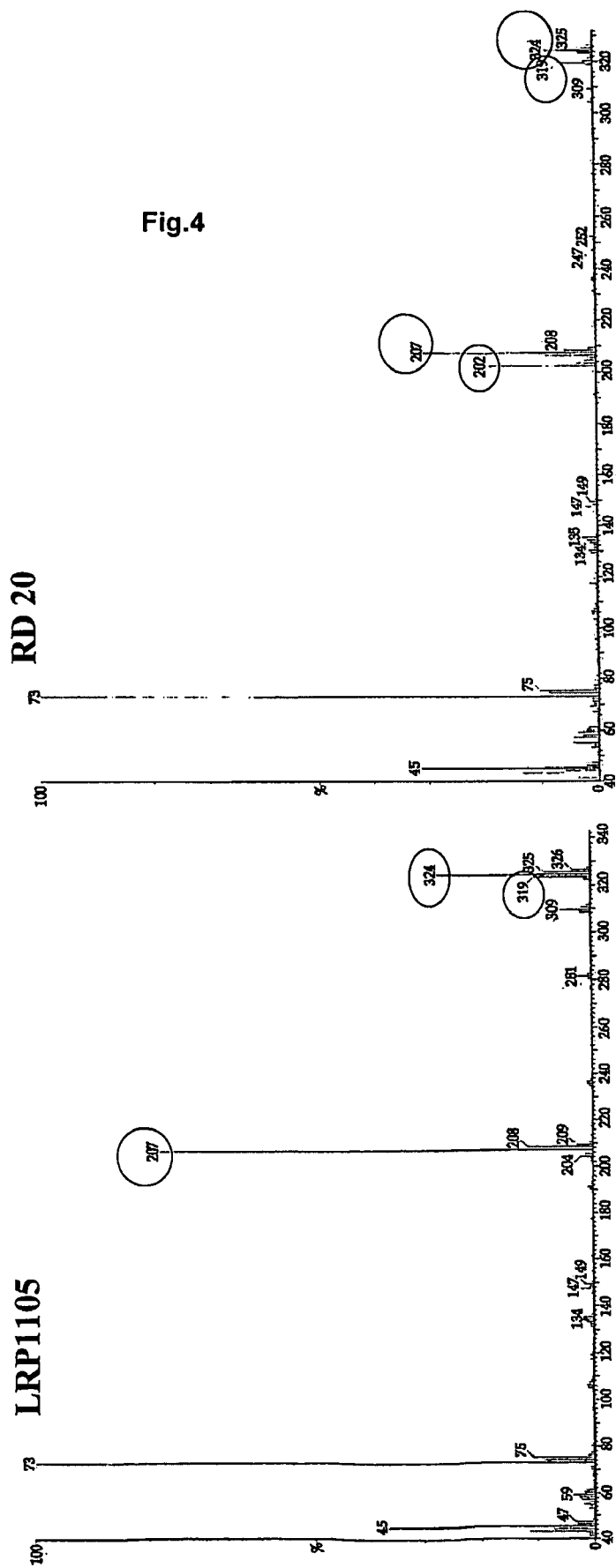

FIG. 4: GC/MS spectrum of nodules of Vicia hirsuta plants infected by the bacterial strains LPR 1105 and RD20. Before the extraction 60 nanomoles of deuterated IAA were added to both samples, then the extracted IAA, conjugate to —Si (CH3)3 to make it volatile, fragment, detected by mass. The peaks related to the integral (319 or 324) or fragmented (202 or 207) IAA are encircled. The deuterated IAA (and the fragments thereof) weigh 5 mass units more than the usual IAA.

Figure 5A:
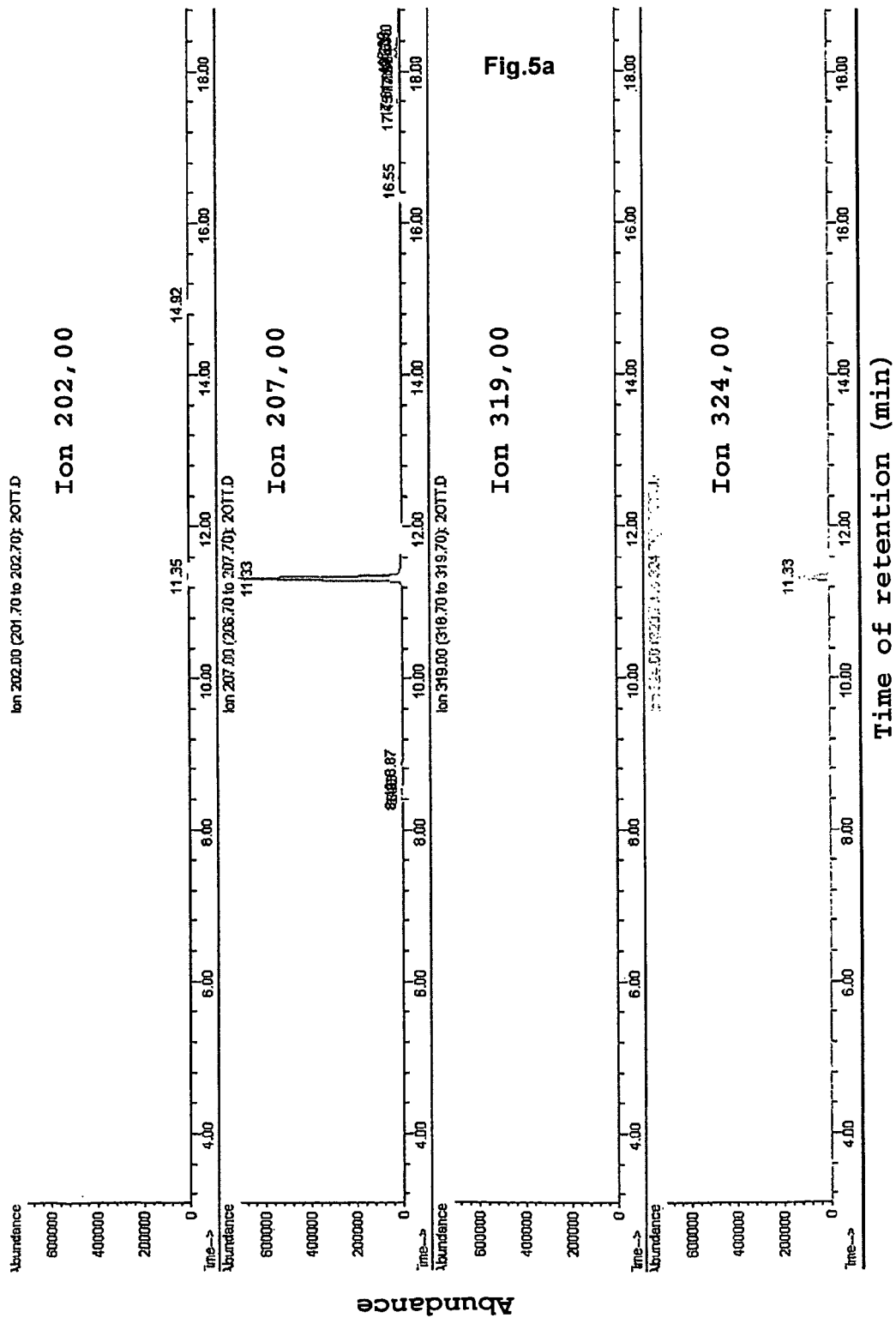
Figure 5B:
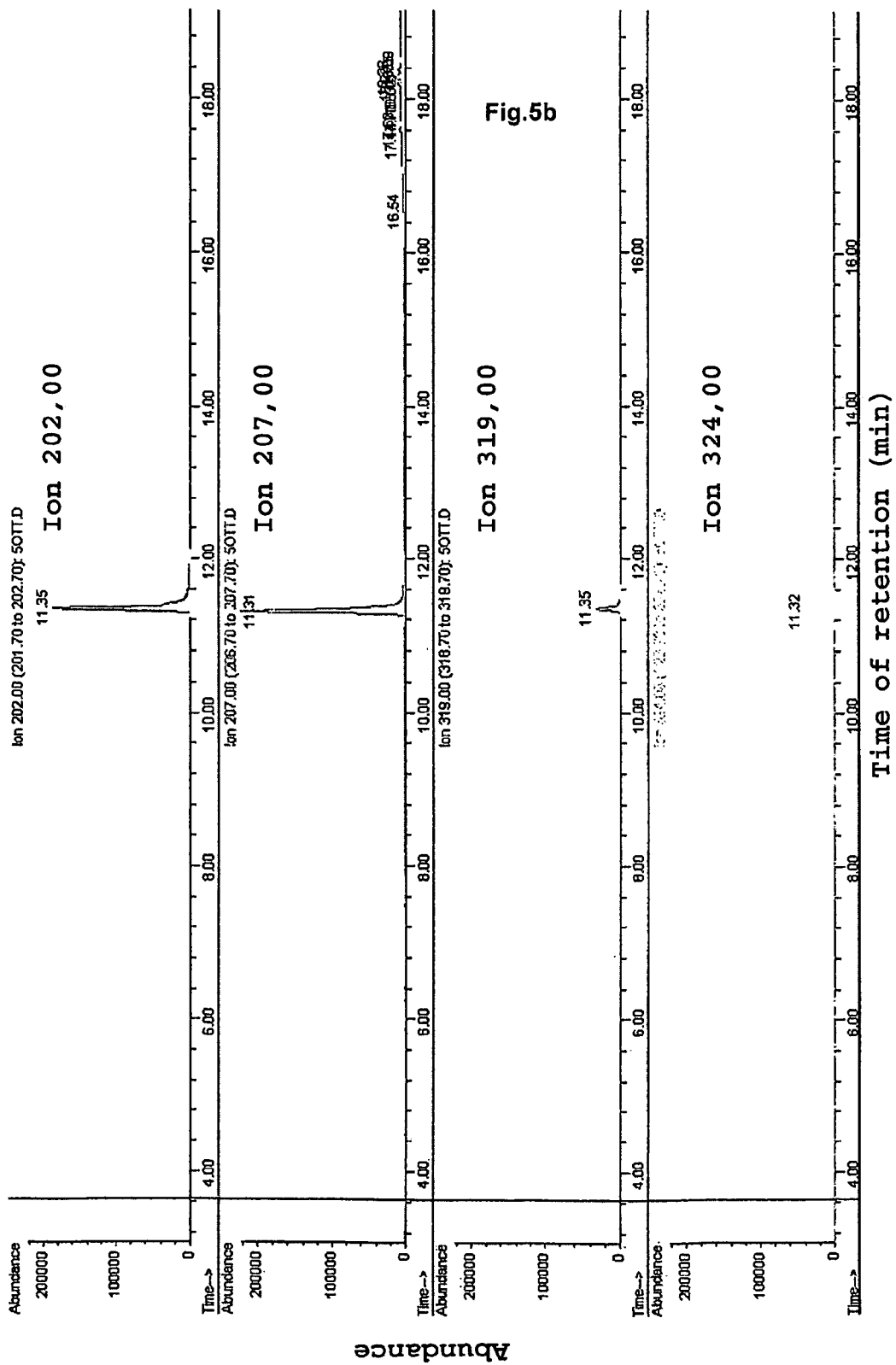

FIG. 5: GC/MS analysis of IAA by the supernatants of the bacterial cultures of wild-type S. meliloti 1021 (FIG. 5a) and of S. meliloti RD 64 (FIG. 5b), after addition of 100 nmoles of D5-IAA.

Figure 6:
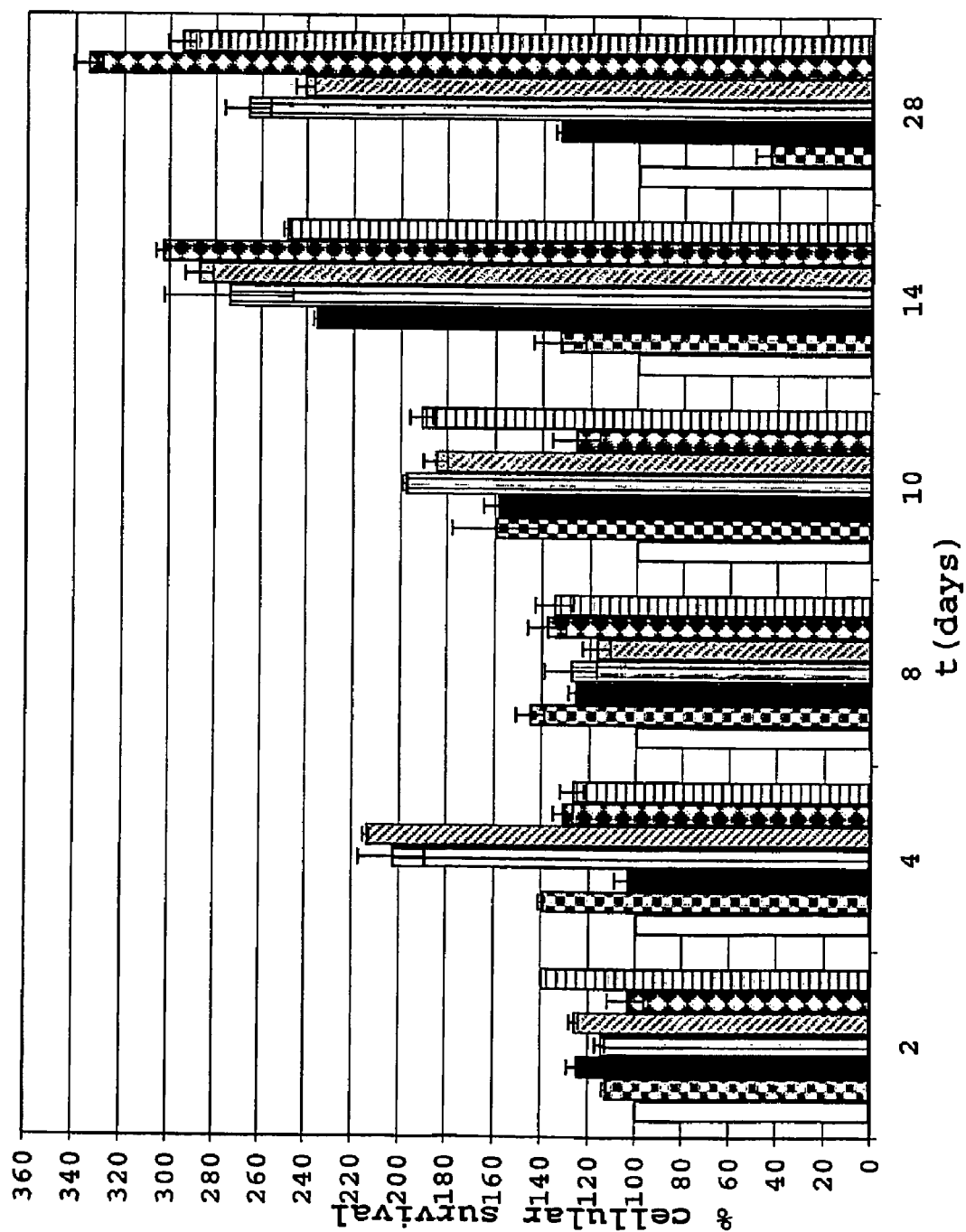

FIG. 6: Effect of the exogenous exposure of IAA to 0.5 mM and 0.05 mM of IAA and of the endogenous production of IAA on the survival of various strains of Sinorhizobium meliloti, wild: 1021, transformed strains: RD 64, 65, 66 and 67.

Figure 7:
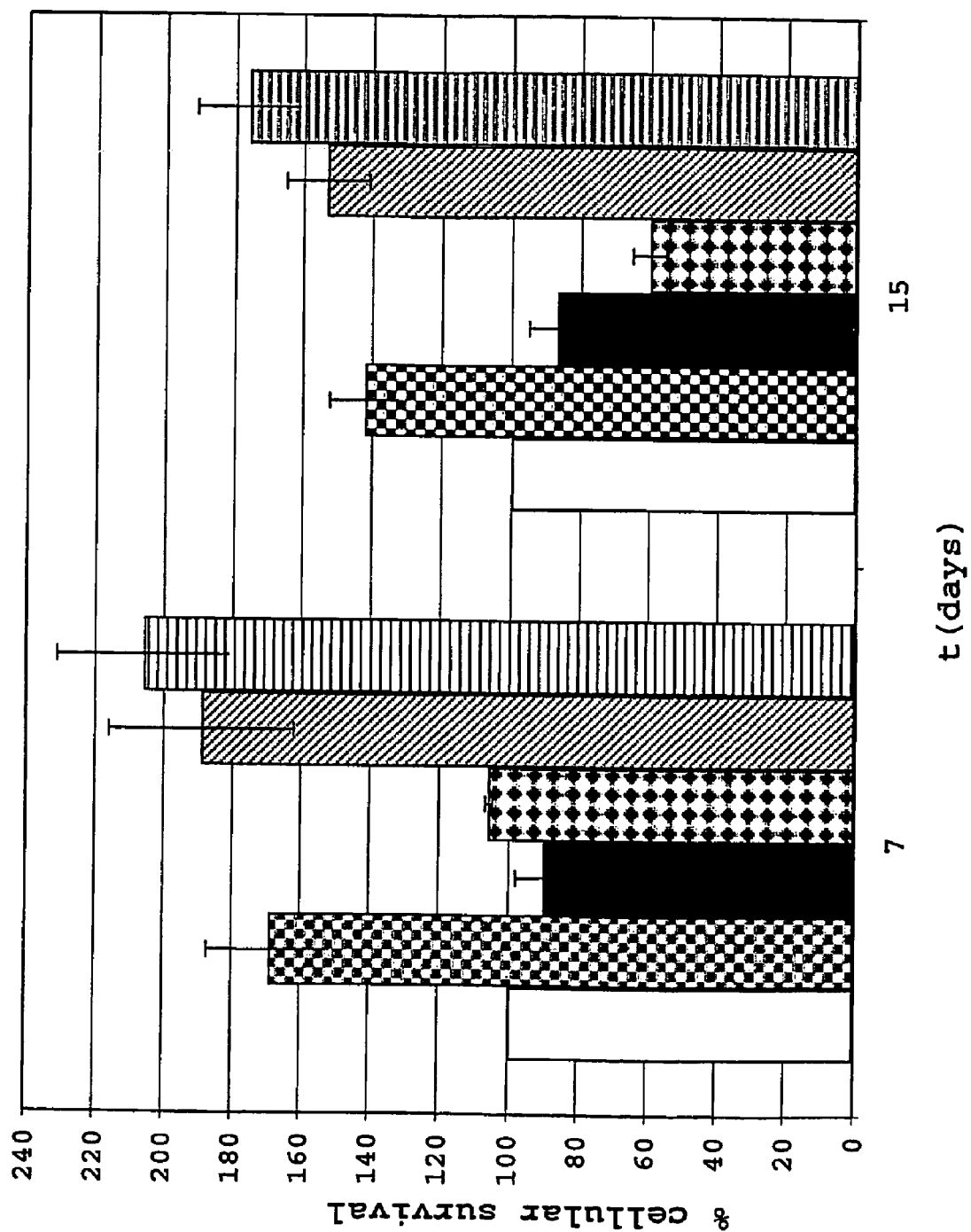

FIG. 7: Effect of the exposure to various doses of exogenous IAA on the survival of wild (1021) and transformed (RD64) Sinorhizobium meliloti.

Figure 8:
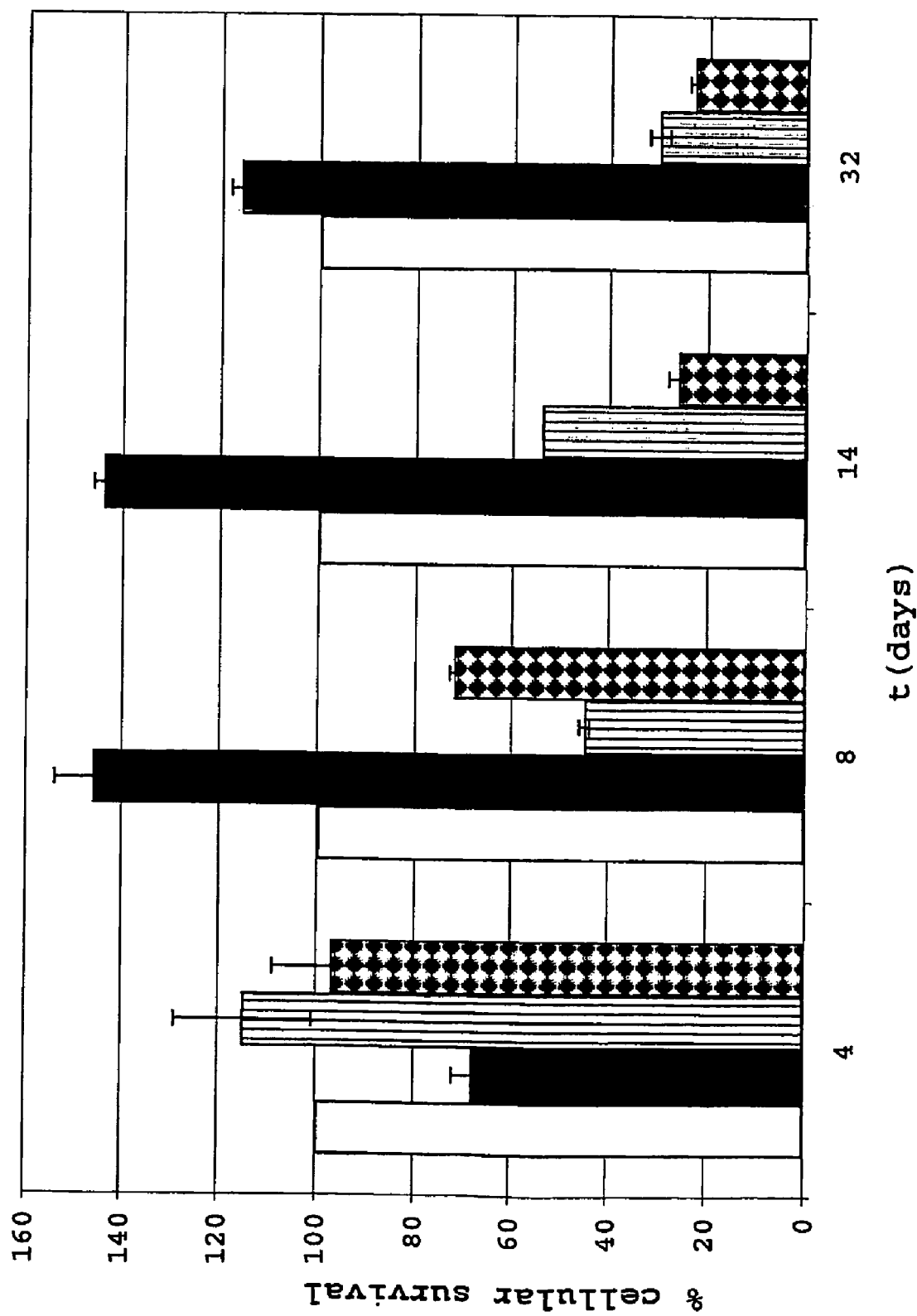

FIG. 8: Effect of a prolonged dehydration on the survival of the various bacterial strains of Sinorhizobium meliloti.

A culture of the wild strain S. meliloti 1021, of the strain 64 and 66 were kept in growth stationary phase for three days, then they were dehydrated vacuum-free and plated at the various times shown in figure. Furthermore, a culture of the wild strain 1021 was subjected to analogous treatment, thereto 0.05 mM IAA were added after two days of growing in stationary phase, the stationary growth continued for a third day and then the bacteria were dehydrated and processed like the preceding samples.

FIG. 9: Survival at 4° C. of wild type S. meliloti 1021 treated with IAA and of the strain RD64. The bacterial cells of the three analysed strains (wild type S.m. 1021, S.m. treated with 0.5 mM IAA and RD64) were grown until exponential phase, then plated and the plates were incubated at 4° C. for 15, 30, 45 and 60 days. Every 15 days, a plate group of each strain was transferred to 30° C. for one day and the colonies were counted.

TABLE 1

Cell resistance of Sinorhizobium meliloti cells to various stress conditions

| Treatment | Survival (%) | | |
|---|---|---|---|
| | 1021 | 1021 + 0.5 mM | 64 |
| Acid shock (pH 3.0) | 0.001 ± 0 | 0.0023 ± 0.0006 | 0.002± |
| Osmotic shock (+0.5 M NaCl) | 49 ± 2 | 78 ± 1 | 90 ± 4 |
| UV-irradiation (100 J/m$^2$) | 67 ± 6 | 86 ± 1 | 92 ± 8 |
| Heat-shock (55° C.) | 0.165 ± 0.005 | 0.196 ± 0.021 | 0.297 ± 0.025 |

The values reported in the Table are the averages±standard deviation of at least five measurements.

MATERIALS AND METHODS

1. Bacterial Strains and Growth Conditions

Rhizobium leguminosarum biovar viciae (LPR1105), a strain derived from RCR1001 (Hooykaas et al), nodulates in a specific way plants of Vicia hirsuta, lentil, broad bean and pea. It is resistant to the rifampicin antibiotic at the concentration of 100 μg/ml. Sinorhizobium meliloti strain 1021 (Galibert et al.) nodulates a variety of lucerne, Medicago truncatula. It is resistant to the streptomycin antibiotic at the concentration of 200 μg/ml. Both bacterial strains, as well as the transformed strains, were grown in minimum medium constituted by: 1% mannitol, 0.1% buffer phosphate pH=7, 0.002% Na2MO4, MnSO4, ZnSO4, 0.002 CuSO4 0.025% MgSO4, 0.002% vitamins (biotin, calcium pantothenate and thiamin), 0.01% NH4Cl, 0.01% CaCl2, 0.0002% CaCl2, 0.001% FeCl3) or in TYR rich medium (tryptone 5 g/l, yeast extract 3 g/l, calcium chloride 6 mM).

2. Mutagenesis and Genetic Engineering

In order to produce IAA by endogenous biosynthetic pathway from the bacterium itself, the author has utilized an engineered bacterium containing a construct with a short promoter sequence (86 pairs of bases) said promintron (Pandolfini et al., 2000) localized upwards two genes (iaaM and tms2) for the biosynthesis of IAA (Seq. Id. No.1). Such construct belongs to a preceding patent (EP Nr. 98830674.2). In order to define the optimum condition for the endogenous IAA production, the author has isolated numerous mutations in the promoter sequence which, once evaluated in indirect way by using the gene reporter GUS, bring to a modulated expression of the beta-glucuronidase (GUS) enzyme (FIG. 1). For this the vector pG was used. The plasmid pG is a derivative of PMB393 (Gage et al.) and it includes the resistance to the spectinomycin antibiotic at the concentration of 200 μg/ml. The different promintron-Gus constructs utilized with the cloning procedure described by Pandolfini et al. were cloned therein. The obtained clones were transferred into bacterial cells of *Rhizobium leguminosarum viciae* LPR1105 and of *S. meliloti* 1021 by transformation by electroporation (Nagel et al.).

a) Transformation of Bacterial Cells with Promintron-Gus Constructs by Means of Electroporation.

The competent cells of *Rhizobium leguminosarum viciae* LPR1105 and of *S. meliloti* 1021 were prepared according to the method described for *Agrobacterium* ssp (Nagel et al.). The clones were purified by means of Qiagen columns. The electroporation was implemented by mixing 40 μl of competent cells with 250 ng of plasmidic DNA pG (Gage et al.) in Bio-RAD cuvettes. The samples were subjected to a 2.5-kV pulse dissipated to 25 μF e 200Ω in the specific Bio-Rad gene pulser instrument. The transformed bacterial cells were selected in TYR rich medium in presence of 200 μg/ml of spectinomycin for the bacterial cells and for the plasmid inserted therein. The transformed strains were controlled by sequencing the plasmids inserted therein.

b) Direct Site Mutagenesis of the Regolative Regions Existing in the Promintron

The reporter constructs utilized to analyse the regolative regions in the promintron were obtained by means of direct site mutagenesis of the 86-17Gus construct (FIG. 1). The oligonucleotides utilized for the amplification reactions by means of PCR were synthesized by the Genset. The outer oligonucleotides correspond to the regions containing the BamHI restriction sites localized at 3' of the 86-17Gus construct, and SnabI positioned inside the Gus gene. These sites were utilized for the subsequent replacement of the amplified portion containing the mutation in the 86-17Gus reporter construct. The inner oligonucleotides include the wished mutation and each pair is complementary.

```
strains RD20 or RD64
                                        (Seq. Id. No 3)
GTGAGTGTGGTTGTAGGTTCAATTATTACTATTTTTGAAGCTGTGTATTT
CCCTTTTTCTAATATGCACCTATTTCATGTTTCAG Mutants 33 or 65
                                        (Seq. Id. No 4)
GTGAGTGTGGTTGTAGGTTCAATTATTACTATTTTTGAAGCTGTGTATTT
CCCTTTTTGACATATGCACCTATTTCATGTTTCAG Mutants 34 or 66
                                        (Seq. Id. No 5)
GTGAGTGTGGTTGTAGGTTCAAGGAGGACTATTTTTGAAGCTGTGTATTT
CCCTTTTTCTAATATGCACCTATTTCATGTTTCAG Mutants 35 or 67
                                        (Seq. Id. No 6)
GTGAGTGTGGTTGTAGGTTCAATTATTACTATTTCCCCAGCTGTGTATTT
CCCTTTTTCTAATATGCACCTATTTCATGTTTCAG
```

| Mutation in promintron-iiaMtms2 | Mutation number | *S. Meliloti* (Sm 1021) | *R. I viciae* (LPR1105) |
|---|---|---|---|
| — | | RD 64 | RD 20 |
| −16/−14 GAC region | 8 | RD 65 | RD 33 |
| −48, 49, 51, 52 G region | 17 | RD 66 | RD 34 |
| −40/−37 CCCC region | 14 | RD 67 | RD 35 |

The mutagenesis were implemented by means of amplification in PCR by using the PfuTurbo DNA Polymerase kit by Stratagene. The amplification reactions were implemented in two phases by using four oligonucleotides. In the first amplification phase, two PCR reactions were implemented in parallel, by using the pair of outer oligonucleotides and an inner pair, containing the wished mutation. The fragments obtained from this first amplification were purified from 2% agarose gel by using the QiaexII kit ("Handbook for DNA extraction from agarose gels" by Qiagen). An amplification product extends from the BamHI restriction site to the site wherein the mutation was introduced, the other one from the SnabI site as far as the mutation site (in Gage et al.). The obtained fragments were used for the second amplification, joined in the same reaction mixture they constitute the DNA template for the outer oligonucleotides. These PCR products are identical to the BamHI-SnabI fragment of the 86-17Gus construct, except for the mutated bases. The fragments containing each one of the mutations were reintroduced in the 86-17Gus reporter vector by using the BamHI and SnabI restriction sites. All so-obtained constructs were controlled by means of sequencing.

c) Determination of Nucleotide Sequences

The sequence reactions were performed by using the Thermo Sequenase Radiolabeled Sequencing kit by USB by following the protocol recommended thereby. The elongation products were interrupted by γ33P-ddNTPs (Amersham Corp. UK). The used triggering oligonucleotides were synthesized by the Genset company.

d) Fluorimetric Gus Assay

The proteins of samples of bacterial cells *R.l. viciae* and *S. meliloti*, containing each promintron-Gus construct, were extracted and assayed in the following manner: 500 μl of bacterial culture picked-up at determined optical densities (0.6 for the exponential phase and 1.5 for the stationary one) were centrifuged and suspended in GBE buffer (phosphate buffer pH=7 50 mM; βeta-mercaptoethanol 10 mM; Na-EDTA pH=8 10 mM; 0.1% sodium dodecyl sulfate SDS; 0.1% Triton X-100). The proteins were extracted by sonication by following the procedure: 20 seconds of sonication and 10 seconds of break for two cycles. The sonicated samples were centrifuged and the supernatant was used for the fluorimetric assay by following the protocol described by (Jefferson). The protein concentration was determined by using the Bradford reagent (BioRad). A microgram of total protein extract was used for the fluorimetric assays. The MUG substrate (4-methylumbelliferylβ-d-glucuronide) was added thereto and the reaction mixture was incubated at 37° C. Three pick-ups at 10', 20' and 30' as from the reaction beginning were performed. The MU (4-methylumbelliferone) reaction product absorbs to UVs in the 365/455 nm range. The activity levels of the Gus protein were expressed in pmol of MU product per minute per milligram of protein (pmolMU/min*mgprotein).

e) Preparation of Promoter-iaaM-tms2 Constructs

The cells of the two wild strains of *Rhizobium leguminosarum bv viciae* LPR1105 and of *S. meliloti* 1021 were transformed with the pG vector (Gage et al. 1996) containing the promintron (Pandolfini et al., 2000) of the rolA gene of *Agrobacterium rhizogenes* (Magrelli, et al.) positioned upwards two genes for the IAA biosynthesis: iaaM and tms2). The first one derives from *Pseudomonas savastanoi p. savastanoi*, whereas the second one derives from *Agrobacterium tumefaciens*. The two genes are an indoleacetamide hydrolase (iaaM) (Yamada et al.) and a tryptophan monooxygenase (tms2) (Klee et al.) which convert the tryptophan into IAA via indoleacetamide, LAM (EP Nr. 98830674.2). In this way, *Sinorhizobium meliloti* 1021 contains a wild promoter short sequence (86 pairs of bases) positioned upwards iaaM and tms2 for the IAA biosynthesis, (strain 64) or it contains a promoter short sequence mutated as indicated:

Sm 1021 containing the promoter-iaaMtms2 construct mutated in the −16/−14 GAC region that is the mutation 8 (see FIG. 1) and hereinafter designated clone 65 in *S. meliloti* and 33 in *R.l. viciae* strain LPR1105;

Sm 1021 containing the promoter-iaaMtms2 construct mutated in the −48, 49, 51, 52 G region, that is the mutation 17 (see FIG. 1) and hereinafter designated clone 66 in *S. meliloti* and 34 in *R.l. viciae* strain LPR1105;

Sm 1021 containing the promoter-iaaMtms2 construct mutated in the −40-37 CCCC region, that is the mutation 14 (see FIG. 1) and hereinafter designated clone 67 in *S. meliloti* and 35 in *R.l. viciae* strain LPR1105;

3. Effect of the iaaM-tms2 Expression on the Sizes of *Rhizobium leguminosarum, Rhizobium viciae* LPR1105 and *S. meliloti* 1021 a) Preparation of the Bacterial Samples for the Electronic Microscope

The strain of wild *Rhizobium leguminosarum biovar viciae* (LPR1105), transformed with the involved construct (RD20), were grown in rich medium (TYR) containing the rifampicin selective antibiotic for the wild bacterial strain and spectinomycin for the RD20 construct.

The collections of aliquots (×100 μl) of the samples were made in different growth phases of the bacterium (stationary and exponential at 0.6 OD).

The collection of bacteria were made in the growth exponential phase, with an optical density (O.D) of 0.62 O.D. or in late stationary phase (the bacteria remained at this O.D. for three days) with an optical density of 1.22 O.D.

b) Transmission Electronic Microscopy (TEM)

The bacteria collected in exponential phase of exponential growth (OD=0.6) were placed onto a copper grid with a 3-mm diameter, which is the support for the TEM, whereon a film of Formvar® (Fluka, code 09818) had been placed previously. The bacteria deposition on the film lasts about one minute; then, a possible bacteria excess is eliminated with filter paper and a dye drop (2% phosphotungstic acid in water at pH 7.00) is added. The reaction stops after few seconds and the dye excess is eliminated with filter paper. The preparation is made to dry and then observed with electronic microscope (Home and Wildy).

The transmission electronic microscope is the Philips EM 208 model with an acceleration voltage of 80 KV and a magnification of 10000×.

4. Effect of the iaaM-tms2 Expression on the Ability of *Rhizobium leguminosarum bv viciae* LPR1105 and *S. meliloti* 1021 to Produce IAA IAA Assay for Mass Spectrometry For the IAA quantitative assay a chromatography technique in gaseous phase, followed by mass spectometry (GC/MS), has been developed. The IAA was extracted according to the method described by Alvarez et al., 1989. 60 nmoles of D5-IAA were added to each sample as inner standard. The extract was dissolved into 100 μl of $CH_3CN$ and treated with 100 μl of N,O-bis-(trimethylsilyl)trifluoroacetamide (BSTFA) as described by Ernsten, et al., 1987. The dried samples were then analysed by GC/MS. The GC analysis was performed by using capillary chromatography columns (J W Scientific DB-5, with a 30-m length, 0.25 mm ED, 0.25-mm thickness of film) and the impact electronic spectrum was obtained starting from a quadripolar mass spectometer TRIO 2000 (Micromass, Manchester, U K).

As inner standard deuterated IAA (D5-IAA) was used, such compound without being radioactive weighs 5 mass units more than the usual IAA the molecular weight thereof is 175. In order to convert such molecule into a gaseous compound, the IAA was derivatized with BSTA (Ernstsen, A et al.) by conjugating to AA the —$Si(CH3)3$, which bring the molecule to 319. D-IAA, then, will weigh 324. For the spectometric analysis the molecule must be fragmented and the main fragmentation originates fragments, respectively, of 202 and 207. Before the extraction, 60 nanomoles of D5-IAA were added in each sample. For each analysis the relationships between the peaks 202+319/207+324 according to the procedure described by Pandolfini et al. are taken into consideration.

The procedure for the supernatant is the same as described for the extracts from the nodules except in that the IAA conjugate hydrolysis lasting three hours, performed soon after the standard addition, is not carried out.

5. Growth and Survival Test a) Effect of the Exogenous Exposition or Endogenous Production of IAA on the Survival of *Sinorhizobium meliloti* 1021

For the growth and survival tests the minimal medium was utilized. A culture of the various strains was kept in growth stationary phase for two days, then they were collected, properly diluted and plated at the various recommended periods of time so as to obtain about 100-1000 colonies per plate. For the strains to be treated with IAA, the addition (0.05 or 0.5 mM IAA) occurred after two days of growth in stationary phase, then the bacteria were diluted and plated.

The author has evaluated the ability of *S. meliloti* 1021 to generate colonies on agar plates after prolonged incubation in growth medium. The formed colonies were counted on at least five plates and the experiment was repeated at least five times.

The number of colonies of not treated *Sinorhizobium meliloti* 1021 was compared to the one of the same strain treated with IAA (0.05 mM and 0.5 mM) two days after reaching the stationary phase of bacterial growth. The percentage value of the surviving cells was measured several days after treatment. Applied stresses were: pH 3 (acid stress): cells were incubated for 30 minutes and then plated; NaCl 0.5 M (high osmotic pressure): 3 hours incubation; UV light resistance: time was not determined but the UV dose was selected to reach an irradiation dosage of 100 $J/m^2$; treatment at high temperature 55° C.: cells were incubated for 5 minutes; treatment at low temperature (4° C.) cells were incubated for up to 60 days at 4° C.

*Sinorhizobium meliloti* 1021 was compared also to the same strain containing a wild promoter short sequence for the IAA biosynthesis, (strain 64) or containing a mutated promoter short sequence (strains 65, 66, 67) as described in Table 1.

In fact, the following groups were compared:
Sm 1021;
Sm 1021 additioned with 0.5 mM IAA;
Sm 1021 additioned with 0.05 mM IAA;
Sm 1021 containing the wild promoter-iaaMtms2 construct (RD 64)
Sm 1021 containing the promoter-iaaMtms2 construct mutated in the −16/−14 GAC region (RD65);
Sm 1021 containing the promoter-iaaMtms2 construct mutated in the −48, 49, 51, 52 G region (RD66);
Sm 1021 containing the promoter-iaaMtms2 construct mutated in the −40-37 CCCC (RD67);

b) Effect of Various IAA Concentrations on the Survival of *Sinorhizobium Meliloti* 1021

In order to evaluate the effect of different IAA concentrations on the survival of *Sinorhizobium meliloti* 1021 the number of colonies generated on agar plates were evaluated (see FIG. 7). The utilized concentrations were 0.05; 0.2; 0.5; and 2 mM IAA. The inocula of the wild strain not treated with IAA were used as controls as well as the RD64 strain. The number of colonies of *S.m.* 1021 was arbitrarily set equal to 100%. The number of colonies generated after 7 and 15 days of growth after the IAA addition in the growth liquid medium was evaluated.

c) Effect of the Dehydration on the Survival of *Sinorhizobium meliloti* 1021

For the dehydration test (FIG. 8), the cells were grown until reaching the stationary phase and kept for 3 days in stationary phase. The cells were centrifuged at 4000 rpm for 15', washed in water and counted on plates as live colonies. The cells were then diluted so as to be aliquoted in Eppendorf tubes at the concentration of 1:10000 for each sample and then vacuum-dried in Savant centrifuge. After 4, 8, 14 and 32 days, the aliquots were plated on TYR selective medium, the formed colonies were counted on at least three plates and the experiment was repeated at least three times.

d) Effect of the Temperature on the Survival of Wild Strain *S. meliloti* 1021 Supplemented with 0.5 mM IAA and of the Strain RD 64

The author has assayed for the bacteria resistance to stresses such as low and high temperatures. For the resistance to high temperatures the cells were grown in exponential phase (optical density 0.6) and then incubated for 2 minutes at room temperature or at 55° C. and then plated.

Furthermore, the author has assayed for the ability of the same strains to resist to prolonged incubations at low temperature (4° C.). The cells of the same three strains: Sm 1021, Sm 1021 treated with 0.5 mM IAA and the strain RD64, were grown until an optical density of 0.6, plated and incubated at 4° C. for periods of time variable up to two months.

6. Cell Resistance of *Sinorhizobium meliloti* Cells to Various Stress Conditions

*Sinorhizobium meliloti* strain 1021 cells and its derivative RD64 overproducing IAA, were exposed to different stress conditions and the number of surviving cells counted by plating opportune dilutions on agar plates; after plates incubation at 30° C., the number of emerging colonies were counted (Table 1).

As a control untreated cells were plated and the number of colonies was considered as 100% for that condition. Stress applied were:
1) low pH, pH 3, treatment: 30 minutes;
2) high osmotic pressure (0.5 M NaCl): 3 hours;
3) UV irradiation were automatically set at 100 J/m$^2$ and cells were irradiate for less that 1 minute;
4) High (55° C.) temperature treatment: 5 minutes.

Results

A) Expression of the Beta-glucuronidase Modulated by the Mutation in the Promoter-iaaMtms2 Sequence The enzymatic assays related to the expression of the GUS gene subjected to the regulation of the wild promintron (strain 1) and of the subsequent 16 mutations (from 2 to 17) in *R.L. viciae* in the exponential and stationary growth phase are shown in FIG. 1. The analysis of the expression of the various mutations has underlined a different gene regulation. The mutations 8, 14 and 17 of the promintron were selected and were positioned upwards the iaaM-tms2 genes to generate respectively the strains RD 33, 34 and 35 in *R.l. viciae* LPR1105 and the strains RD 64, 65 and 66 in *S. meliloti* 1021. Analogous experiments were performed in *S. meliloti* and in *Rhizobium etli* (the strain which nodulates bean plants) with similar results.

B) Bacterial Morphology Analysed by Electronic Microscope

FIG. 2 shows that the wild bacterial strain *Rhizobium leguminosarum biovar viciae* (LPR1105) in growth stationary phase is significantly longer than its derivative RD20 engineered with the promoter-iaaMtms2 construct. This occurs also for the bacteria derived from *S. meliloti*. The transformed strains RD20 (*R.l. viciae*) and 64 (*S. meliloti*) show a more rounded and shortened phenotype with respect to the corresponding wild strains. This testifies that the greater IAA production alters the shape of the bacterium by making the bacterium smaller and probably metabolically more active than the parental strain thereof.

C) IAA Quantitative Analysis

In case of the supernatant of LPR1105 cells, the latter show an increase 10 times higher than the IAA concentration (FIG. 3). Such increase rises to 60 times (2 nmoles against 120 nanomoles) in case of IAA extracted from root nodules after 33 days of life extracted from pea plants nodulated from the strain RD20 with respect to analogous nodules generated from the wild strain LPR1105 (FIG. 4).

In the case of the wild bacterial strain *S. meliloti* 1021 and of the strain RD64, the latter shows a IAA concentration up to 80 times greater than the control.

D) Effect of the Transformation of S. meliloti 1021 on the Survival

The strains RD 64 and 65 show a greater ability to generate colonies with respect to the reference strain (1021) in brief times (4 days, FIG. 6). In longer times, the strains 64 and 65 confirm able to allow a good survival of the bacterial cells (FIGS. 6 and 7).

E) Effect of the Exogenous Exposition or the Endogenous Production of IAA on the Survival of *Sinorhizobium meliloti* 1021

The addition of 0.5 and 0.05 mM of IAA induces a greater ability to generate colonies with respect to the reference strain (1021) (FIG. 6). The use of various IAA concentrations (FIG. 7) confirms that the IAA addition at the 0.5 mM and 0.2 mM concentrations is effective to increase the ability to generate colonies.

F) Effect of the Dehydration on the Survival of *Sinorhizobium meliloti* 1021 and Transformed Strains RD 64 and Rd66

It can be observed that under the analysis conditions the treatment with IAA at 0.05 mM increases the survival of the bacterical cells up to 50%. On the contrary, the total dehydration damages to the strains 64 and 66 more than to the wild strain 1021 (FIG. 8).

G) Resistance to Unfavourable Temperatures by Strains of *S. meliloti* 1021

As far as the resistance to the heat shock is concerned, cells of the wild strain *S. meliloti* 1021 were compared to the same cells exposed to 0.05 mM IAA and the latter showed a greater resistance by generating colonies up to 20% more than the control. Such resistance is greater in the strain RD64 which generates colonies up to 80% more than the strain *S.m.* 1021 (see Table 1).

The values in the days shown in FIG. 9 refer to the number of days therefor the plates were incubated at 4° C. before being transferred for two days at 30° C. to allow to the live cells to generate colonies. FIG. 9 underlines that the number of cells able to generate colonies after 45 and 60 days of incubation at 4° C. is almost the double in case of the wild strain (Sm 1021) treated with 0.5 mM IAA with respect to the same not treated strain. For the strain RD64 the increase in the live cells able to generate colonies has increased by about 50% with respect to the wild strain Sm 1021. Therefore, in the wild strain RD64 or in the wild strain treated with IAA an increase in colonies resistant to a treatment of "heat shock" with respect to the cells of the wild strain *Sinorhizobium meliloti* 1021 can be observed.

In Table 1 is indicated that strain RD64 and IAA-treated strain 1021 are 100% more resistant that the untreated 1021 when cells are exposed for 30 minutes to a very low pH (pH3). In addition Iaa-treated 1021 strain and RD 64 are more resistant than the untreated 1021 strain when challenged in a high osmotic solution (50% and 80% respectively), to an intense UV irradiation (10% and 20% respectively), to high temperature as 55° C. (10% and 80% respectively).

CONCLUSIONS

The described method testifies that: a) the transformed strains synthesize IAA 10 times more than their untransformed correspondents and that such concentration increases up to about 60 times more when the root nodules are evaluated; b) the promoter mutagenesis alters the synthesis levels of the genes subjected to the control of said promoter; c) upon a greater IAA synthesis (or by adding purified IAA at the 0.5 mM concentration) there is a total increase in the number of live cells in liquid culture of at least 100% with respect to the wild strain after two growth weeks; d) by using an equal number of pelleted, dehydrated and plated cells at increasing times, an additional increase in the cellular survival up to 40% can be obtained after two weeks in case of the strain cultivated with the addition of IAA purified at 0.05 mM.

BIBLIOGRAPHY

Brill, W. J. Biology of nitrogen fixation. Sci. Am. 236, 68-81 (1977).

Yamada, T., Curtis, J. P., Brooks, B. & Kosuge, T. Nucleotide sequences of the *Pseudomonas savastanoi* indoleacetic acid genes show homology with *Agrobacterium tumefaciens* T-DNA. Proc. Natl. Acad. Sci. USA 82, 6522-6526 (1985).

Klee, H. et al. Nucleotide sequence of the tms genes of the pTiA6NC octopine Ti plasmid: two gene products involved in plant tumorigenesis. Proc. Natl. Acad. Sci. USA 81, 1728-1732 (1984).

Ernstsen, A., Sandberg, G., Crozier, A. & Wheeler, C. T. Endogenous indoles and biosynthesis and metabolism of indole-3-acetic acid in cultures of *Rhizobium phaseoli*. Planta 171, 422-428 (1987).

Hirsch, A. M., Fang Y., Asad S. & Kapulnik Y. The role of phytohormones in plant-microbe symbioses. Plant and Soil 194, 171-184 (1997).

Pandolfini T., Storlazzi A., Calabria E., Defez R., Spena A. The splicesomal intron of the rolA gene of *Agrobacterium Rhizogenes* is a prokariotic promoter. Molecular Microbiology, 2000. 35: p. 1326-1334.

Pandolfini T, Rotino G L., Camerini S, Defez R, Spena A., Optimisation of transgene action at the post-transcriptional level: high quality parthenocarpic fruits in industrial tomatoes BMC Biotechnology (2002) 2:1 (11 Jan. 2002) online at http://www.biomedcentral.com/1472-6750/2/1/.

A. Magrelli, K. Langenkemper, C. Dehio, J. Schell, A. Spena Splicing of the rolA transcript of *Agrobacterium rhizogenes* in Arabidopsis. Science, 1994. 266: p. 1986-1988.

Gage D. J., T. Bobo, and S. R. long Use of green fluorescent protein to visualize the early events of symbiosis between *R. meliloti* and alfalfa (*Medicago sativa*). Journal of Bacteriology, 1996. 178: p. 7159-7166.

Galibert F., T. M. Finan, S. R. Long, A. Puhier, P. Abola, F. Ampe, F. Barloy-Hubler, M. J. Barnett, A. Becker, P. Boistard, G. Bothe, M. Boutry, L. Bowser, J. Buhrmester, E. Cadieu, D. Capela, P. Chain, A. Cowie, R. W. Davis, S. Dreano, N. A. Fedespiel, R. F. Fisher, S. Gloux, T. Godrie, A. Goffeau, B. Golding, J. Gouzy, M. Gurjal, I. Hernandez-Lucas, A. Hong, L. Huizar, R. W. Hyman, T. Jones, D. Kahn, M. L. Kahn, S. Kalman, D. Masuy, C. Palm, M. C. Peck, T. M. Pohl, D. Portetelle, B. Purnelle, U. Ramsperger, R. Surzycki, P. Thebault, M. Vandenbol, F. J. Vorholter, S. Weidner, D. H. Wells, K. Wong, K. C. Yeh, J. Batut. The composite genome of the legume symbiont *Sinorhizobium meliloti*. Science, 2001. 293: p. 668-672.

Hooykaas P. J. J., P. M. Clapwijk, M. P. Nuti, R. A. Shilperoort, and A. Roersch Transfer of the *Agrobacterium tumefaciens* Ti plasmid to virulent *Agrobacteria* and to *Rhizobium* ex-planta. J. Gen. Microbiology, 1977. 98: p. 477-484.

Horne R W and Wildy P (1979). Journal of Microscopy, 117, 103

Nagel R. A., A. Eliott, A. Masel, R. G. Birch, and J. M. Manners Electroporation of binary Ti plasmid vector into *A. thumefaciens* and *A. rhizogenes*. FEMS Lett., 1990. 67: p. 325-328.

Jefferson, R. Assaying chimeric genes in plant: the Gus gene fusion system. Plant Molecular Biology, 1987. 5: p. 387-405.

Alvarez, R., Nissen, S. J., and Sutter, E. G. Relationship between indole-3-acetic acid levels in apple (Malus pumila Mill) rootstocks cultured in vitro and adventitious root formation in the presence of indole-3-butyric acid. Plant Phisiol. 89, 439-443 (1989).

The invention claimed is:

1. A method for increasing the survival of bacteria of the *Rhizobium* genus or of the *Sinorhizobium meliloti* species comprising the steps of:
   a) making the bacteria to grow in a chemically defined culture medium;
   b) keeping the bacteria in growth stationary phase;
   c) exposing the bacteria to effective quantities of exogenous indole-3 acetic acid (IAA).

2. The method according to claim 1 wherein the bacteria are kept in growth stationary phase for at least 48 hours.

3. The method according to claim 1, wherein the exogenous IAA concentration between 0.05 mM and 2 mM.

4. A method for increasing the survival of bacteria of the *Rhizobium* genus or of the *Sinorhizobium meliloti* species by means of genetic engineering comprising the steps of:
   a) transforming said bacteria with a recombinant vector comprising polynucleotides encoding indoleacetamide hydrolase and tryptophan monooxygenase and effectively expressing them;
   b) making the bacteria to grow in chemically defined culture medium;
   c) keeping the bacteria in growth stationary phase.

5. The method according to claim 4 wherein the bacteria are kept in growth stationary phase for at least 48 hours.

6. The method according to claim 1 or 4, wherein the bacteria of the *Rhizobium* genus belong to the *Rhizobium leguminosarum biovar viciae* specie.

7. The method according to claim 4, wherein the polynucleotides encoding indoleacetamide hydrolase and tryptophan monooxygenase are under the regulatory control of an *Agrobacterium rhizogenes* rolA gene promintron.

8. The method according to claim 7, wherein the *Agrobacterium rhizogenes* rolA gene promintron is a mutated promintron selected from the group consisting of (a) a −16/−14 GAC region mutant. (b) a −48, 49, 51, 52 G region mutant, and (c) a −40-37 CCCC region mutant.

* * * * *